United States Patent [19]

Erbel et al.

[11] Patent Number: 5,205,287
[45] Date of Patent: Apr. 27, 1993

[54] ULTRASONIC CONTRAST AGENTS, PROCESSES FOR THEIR PREPARATION AND THE USE THEREOF AS DIAGNOSTIC AND THERAPEUTIC AGENTS

[75] Inventors: Raimund Erbel; Rainer Zotz, both of Mainz; Volker Krone, Flörsheim; Michael Magerstädt, Hofheim am Taunus; Axel Walch, Frankfurt am Main, all of Fed. Rep. of Germany

[73] Assignee: Hoechst Aktiengesellschaft, Frankfurt am Main, Fed. Rep. of Germany

[21] Appl. No.: 955,146

[22] Filed: Oct. 1, 1992

Related U.S. Application Data

[62] Division of Ser. No. 859,257, May 26, 1992, which is a division of Ser. No. 690,761, Apr. 24, 1991, Pat. No. 5,137,928.

[30] Foreign Application Priority Data

Apr. 26, 1990 [DE] Fed. Rep. of Germany ....... 4013231

[51] Int. Cl.$^5$ .......................... A61B 5/00; A61B 8/00; A61B 17/20
[52] U.S. Cl. .............................. 128/632; 128/660.01; 128/660.02; 128/660.03; 424/9; 604/22
[58] Field of Search ............... 424/9; 128/632, 653 R, 128/660.01, 660.02, 660.03; 604/22

[56] References Cited

U.S. PATENT DOCUMENTS

| | | |
|---|---|---|
| 4,276,885 | 7/1981 | Tickner et al. . |
| 4,906,473 | 3/1990 | Bader et al. . |
| 5,041,291 | 8/1991 | Bader et al. . |

FOREIGN PATENT DOCUMENTS

| | | |
|---|---|---|
| 0122624A2 | 10/1984 | European Pat. Off. . |
| 0123235A2 | 10/1984 | European Pat. Off. . |
| 0224934A2 | 6/1987 | European Pat. Off. . |
| 0274127A2 | 12/1987 | European Pat. Off. . |
| 0327490A1 | 8/1989 | European Pat. Off. . |
| 4002736.8 | 10/1990 | Fed. Rep. of Germany . |

OTHER PUBLICATIONS

R. A. Levine, et al., "Microbubbles Have Intracardiac Velocities Similar to Those of Red Blood Cells," J. Am. Coll. Cardiol., 3(1):28-33 (1989).

I. Machi, et al., "Relation of In Vivo Blood Flow to Ultrasound Echogenicity," J. Clin. Ultrasound, 11:3-10 (1983).

German Patent Application No. 40 02 736.8 filed Jan. 31, 1990.

*Primary Examiner*—Morton Foelak
*Attorney, Agent, or Firm*—Finnegan, Henderson, Farabow, Garrett & Dunner

[57] ABSTRACT

The invention relates to ultrasonic contrast agents composed of microparticles which contain a gas and polyamino-dicarboxylic acid-co-imide derivatives, to processes for their preparation and to their use as diagnostic and therapeutic agents.

3 Claims, No Drawings

ULTRASONIC CONTRAST AGENTS, PROCESSES FOR THEIR PREPARATION AND THE USE THEREOF AS DIAGNOSTIC AND THERAPEUTIC AGENTS

This is a division of application Ser. No. 07/859,257, filed May 26, 1992, which is a division of application Ser. No. 07/690,761, filed Apr. 24, 1991, now U.S. Pat. No. 5,137,928.

The invention relates to ultrasonic contrast agents composed of microparticles which contain a gas and polyamino-dicarboxylic acid-co-imide derivatives, processes for their preparations and their use as diagnostic and therapeutic agents.

Ultrasonic diagnosis has become very widely used in medicine because it is complication-free and straightforward to perform. Ultrasonic waves are reflected at interfaces of different types of tissue. The echo signals produced thereby are electronically amplified and displayed.

Visualization of blood vessels and internal organs by ultrasound does not in general allow visualization of the blood flow present therein. Liquids, especially blood, provide ultrasonic contrast only when there are density differences with respect to the surroundings. Used as contrast agents in medical ultrasonic diagnosis are, for example, substances which contain gases or produce gases, because the difference in impedance between gas and surrounding blood is considerably greater than that between liquids or solids and blood (Levine R.A., J Am Coll Cardiol 3:28, 1989; Machi I.J. CU 11: 3, 1983).

Several methods for preparing and stabilizing gas bubbles are disclosed in the literature. U.S. Pat. No. 4,276,885 describes the preparation of small gas bubbles of defined size which are enclosed by a gelatin casing which prevents coalescence of the gas bubbles. The prepared small gas bubbles can be stored only in the frozen state, and the small gas bubbles must be returned to body temperature for use.

EP-A2 0,123,235 and 0,122,624 describe ultrasonic contrast agents which contain gases and are composed of mixtures of surface-active substances with a solid in a liquid vehicle. The ultrasonic contrast agents are prepared by an elaborate millint process with an air-jet mill. The particles prepared in this way have only a short duration of use because they rapidly lose the entrapped gases.

EP-A2 0,224,934 describes ultrasonic contrast agents in the form of gas-filled gelatin or albumin hollow bodies. However, the disadvantage is the use of exogenous or denatured endogenous proteins because of the allergenic risk associated therewith.

AP-A1 0,327,490 describes microparticles which are composed of amyloses or snythetic, biodegradable polymers and of a gas and/or a liquid with a boiling point below 60° C. The disadvantages of these polymers are their sticky consistency in water or blood, their poor biodegradability, their toxicity or the production of toxic degradation products.

It has already been proposed (German Patent Application P 40 02 736.8) to employ polyamino-dicarboxylic acid-co-imide derivatives as biodegradable depot formulations of pharmaceuticals with controlled release of active substance.

The object of the present invention was to develop ultrasonic contrast agents based on microparticles, which provide a distinct contrast from the surrounding tissue, which are so small and stable that they reach, without considerable loss of gas and essentially quantitatively, the left half of the heart after intravenous administration, are well tolerated without an allergenic potential, do not form aggregates in water or blood, and can be prepared rapidly and straightforwardly.

Microparticles which are, surprisingly, outstandingly suitable as ultrasonic contrast agents have been prepared from polyamino-dicarboxylic acid-co-imide derivatives (polydicarboxylic acid-co-AHADA derivatives). In particular, the amenability of the prepared microparticles to be suspended in water is outstanding owing to the incorporation of unopened imide rings (AHADA rings). The microparticles do not have a sticky, greasy consistency in water-containing liquids and form scarcely any agglomerates. The polymers form a pharmacologically inert matrix in which the gas is entrapped. In vivo, these polymers are metabolized to non-toxic, non-allergenic and non-immunogenic compounds and are excreted. It was possible to show in animal experiments that the microparticles essentially pass through the lungs without significant loss of gas and result in an ultrasonic contrast of equal intensity in both halves of the heart. The echocardiograms recorded therewith show no wall-movement disturbances whatever during and up to 60 min after administration of the contrast agent. Furthermore, it was not possible to find any changes whatever in a six-channel ECG or in the contractility determined using a tip manometer.

The ultrasonic contrast agents according to the invention bring about an improved increase in echogenicity in the myocardium and permit improved visualization of the endocardium. It is furthermore possible for example, to assess the following parameters better: ventricle size, wall-movement disturbances, stroke volume, ejection fraction or intracavitary masses, for example thrombi or tumors. Furthermore, the ultrasonic contrast agents according to the invention make it possible to evaluate flow patterns in cases of valvular insufficiency of the left and of the right half of the heart, intracardiac shunts, and improved visualization of the large vessels in cases of congenital malformation. A massive enhancement of the Doppler signal has also been observed.

The invention thus relates to ultrasonic contrast agents composed of microparticles which contain a gas and a polyamino-dicarboxylic acid-co-imide derivative of the formula I,

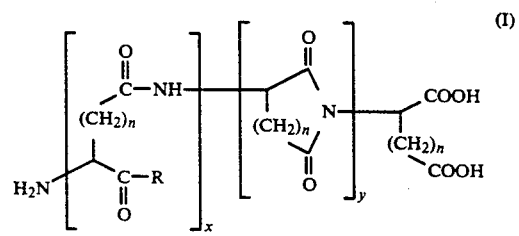

in which
  n is 1 or 2
  x is 1 to 500
  y is 1 to 500, where
  x+y is 2 to 1000, and
  R is O—$R^1$ or NH—$R^2$, in which
    $R^2$ is H, $(CH_2)_m$—$OR^1$, $(CH_2)_m$—O—C(O)—$R^1$ or $(CH_2)_m$—O—C(O)—$OR^1$, and m is 2 to 6, and R¹ is H, aryl, aralkyl, arylalkenyl, alkyl or $C_3$-$C_8$-cycloalkyl or a biologically inactive steroid alcohol or an amino acid, where aryl is unsubstituted or is substituted by $C_1$-$C_4$-alkyl, $C_2$-$C_4$-alkenyl, $C_1$-$C_4$-alkylcarbonyloxy, $C_1$-$C_4$-alkoxy or hydroxyl, where the alkyl radicals specified for R¹ have 1-22 carbon atoms and the alkenyl radicals have 2-22 carbon atoms, which are not interrupted or are interrupted by a carbonyloxy or oxycarbonyl group, where the repeating units placed in square brackets are distributed randomly and/or in blocks in the polymer, and where both the repeating units labeled with x and those labeled with y are identical or different and where the amino acids are α- and/or β-linked.

By aryl are meant aromatic hydrocarbons such as phenyl and naphthyl, especially phenyl. In the substituted aryl radicals indicated, 1 to all replaceable hydrogen atoms are replaced by identical or different substituents. The aryl radicals are preferably mono- or disubstituted.

The said alkyl and alkenyl radicals can be both straightchain and branched.

The biologically inactive steroid alcohols are preferably linked via their OH group. A preferred steroid alcohol is cholesterol.

In the case of the amino acids specified for R¹, they are preferably naturally occurring amino acids such as Tyr, Ala, Ser or Cys, particularly preferably Tyr and Ala. They can be linked both via their $NH_2$ and via their COOH group.

The invention also relates to processes for the preparations of gas-containing microparticles which are composed of the abovementioned polymers or contain these, and to their use, also mixed with other, biocompatible and/or biodegradable polymers or physiologically acceptable auxiliaries, for diagnostic or therapeutic procedures.

The invention further relates to diagnostic or therapeutic agents composed of at least one ultasonic contrast agent as claimed in one or more of claims 1 to 4 or of at least one ultrasonic contrast agent prepared by a process which comprises:

(a) a solution of one or more polyamino-dicarboxylic acid-co-imide derivatives of the formula I or a solution of this or these derivatives which additionally contains one or more other polymers and/or physiologically acceptable auxiliaries being spray-dried, or (b) one or more polyamino-dicarboxylic acid-co-imide derivatives of the formula I being dissolved in a solvent or solvent mixture with high melting point, or these derivatives being mixed with one or more other polymers and/or physiologically acceptable auxiliaries and dissolved in a solvent mixture with high melting point and then added dropwise to a condensed cold gas and subsequently the solvent being removed, or (c) one or more polyamino-dicarboxylic acid-co-imide derivatives of the formula I being dissolved in a solvent or solvent mixture and subsequently, where appropriate after addition of another solvent and/or of one or more other polymers, being precipitated or dispersed in water, and the resulting suspension being freed of solvents.

The invention additionally relates to processes for the preparation of diagnostic or therapeutic agents, which comprise converting the abovementioned ultrasonic contrast agents with a physiological vehicle and, where appropriate, further additives and/or auxiliaries into a suitable administration form.

The invention is described in detail hereinafter.

Aspartic acid and/or glutamic acid are employed as amino dicarboxylic acids which react in a polycondensation reaction to give the corresponding polymides (polyanhydro-amino-dicarboxylic acids, formula II). Partial reaction with one or more compounds of the formulae III and/or IV and/or $NH_3$

HO—R¹ tm (III)

$H_2N$—$(CH_2)_m$—OH (IV), in which m and R¹ are defined as above for formula I, results in an α, β-poly-D,L-amino acid ester-co-imide of the formula VIII

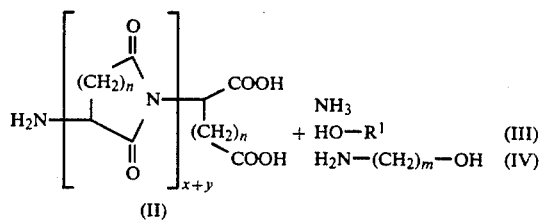

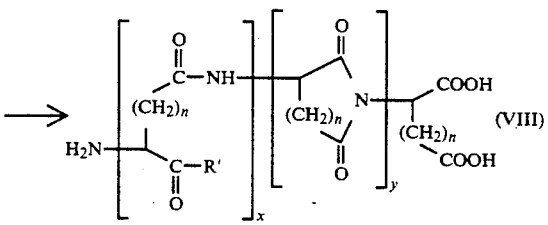

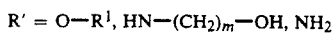
R' = O—R¹, HN—$(CH_2)_m$—OH, $NH_2$

It is essential that in this reaction the polyanhydroamino-dicarboxylic acid (II) is only partially converted into the open-chain derivatives. The proportion of unopened anhydro-amino-dicarboxylic acid units is 0.1 to 99.9%, preferably 10 to 90% (the percentages relate to the total number of repeating units in the total polymer). Depending on the side on which the imide ring is opened in the reaction described above, α- or β-linked amino acids are obtained. Compounds of the formulae III and IV which are preferably employed are: 2-aminoethanol, 3-aminopropanol, 2-aminopropanol, alcohols with 1-18 carbon atoms, especially methanol, ethanol, isoamyl alcohol and isopropyl alcohol.

A process for the preparation of α, β-poly-(2-hydroxyethyl) -DL-aspartimide (PHEA) (formula I; y=0; R=NH—$CH_2$—$CH_2$—OH) is described by P. Neri, G. Antoni, F. Benvenuti, F. Cocola, G. Gazzei, in J. Med. Chem. Vol. 16, 893 (1973). A general procedure for the preparation of PHEA is to be found in P. Neri, G. Antoni, Macromol. Synth. Vol. 8, 25. Express reference is made to this citation at this point. The reaction takes place in high yield to give a product of high purity. It is possible to prepare in the same way, by less than stoichiometric use of $NH_3$ and/or compounds of the formulae III and/or IV, the analogous poly-aspartic acid derivative-co-succinimide compounds of the formula VIII (n=1).

A different more elaborate process as is described in U.S. Pat. No. 4,356,166 must be used to prepare pur poly(hydroxyalkyl)-L-glutamine. this entails initially the γ-COOH group of the L-glutamic acid being protected by esterification with benzyl alcohol. This γ-benzyl glutamate is subsequently reacted with phosgene to give an N-carboxylic anhydride which then polymerizes after addition of triethylamine in an inert solvent to result in poly-γ-(benzyl)-L-glutamate. The protective group is eliminated either by adding an HCl/HBr mixture to give the free poly-α-L-glutamic acid or else in the presence of hydroxyalkylamines to give the analogous poly-60 -(hydroxyalkyl)-L-glutamines. A general procedure for the preparation of poly-α-(hydroxypropyl)-L-glutamine is to be found in U.S. Pat. No. 4,356,166, to which express reference is made at this point. It is also possible in the same way, by using $NH_3$ and/or compounds of the formula III and/or IV, to prepare the analogous compounds of the formula VIII (n=2).

Compared with the elaborate preparation of pur polyglutamic acid and its derivatives, it is possible to incorporate glutamic acid in up to high proportions on simple condensation of aspartic acid using phosphoric acid to give polyanhydroaspartic acid-co-glutamic acid.

The polyamino-aminde-co-imides of the formula VIII (R'=HN— $(CH_2)_m$—OH) can now, if necessary, be reacted in the following reaction step with one or more different biologically inactive compounds of the formula V and/or VI and/or VII

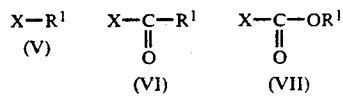

to give further polyamino-dicarboxylic acid-co-AHADA derivatives. In this case X is a leaving group which allow mild esterification of the polymer alcohol group. Chlorine, bromine, iodine, imidazolides, anhydrides or hydroxyl, especially chlorine, are preferred.

The reaction with the compounds of the formula V, VI or VII type can be carried out both with a single compound of this type and with any desired combinations of these compounds, or else with compounds which have different radicals $R^1$, for example differing in the nature of their branching, in particular in their chain length.

The last-mentioned alkylation or acylation on the polymer is carried out by known processes of organic chemistry. It takes place selectively on the hydroxyl group (formula VIII, R'=HN—$(CH_2)_m$—OH) to give ethers, ethers, or carbonates without attacking other groups on the initial polymer. Particularly suitable is the Einhorn variant of the Schotten-Baumann acylation in the presence of pyridine. In this case, very high levels of derivitization (greater than 70%) are achieved under mild conditions.

The molecular weight of the polymers is 200 to 100,000, preferably 3,000 to 70,000.

Compounds of the formula V type can be bought or, if not, synthesized in a straightforward manner by processes known from the literature.

The chloroformic esters (formula VII) are obtained by reacting phosgene with the appropriate biologically inactive, physiologically acceptable, aromatic, araliphatic, aliphatic or cycloaliphatic, especially unbranched alcohols. The alcohols which are particularly preferably employed are those which have an even number of carbon atoms. The chloroformylated steroids are also obtained in this way. Thus, in principle, all biologically inactive steroids having reactive hydroxyl groups can be obtained. Examples which may be mentioned here are: cholesterol, cholestanol, coprostanol, ergosterol, sitosterol or stigmasterol.

The acid chlorides (formula VI) which can likewise be employed are obtained, for example, from the corresponding carboxylic acids by reaction with phosphorus trichloride, phosphorus pentachloride, oxalyl chloride or thionyl chloride.

Compounds of the formula V, VI or VII type in which an alkyl chain is interrupted by an oxycarbonyl or carboyloxy group are prepared, for example, by reaction of cyclic dicarboxylic acid anhydrides with alcohols. The dicarboxylic monoesters obtained in this way are then reacted in analogy to the carboxylic acids described above, for example with oxalyl chloride, to give the corresponding acid chlorides.

An advantageous process for the preparation of the ultrasonic contrast agents comprises dissolving one or more of the polyamino-dicarboxylic acid-co-imide derivatives of the formula I in a solvent or solvent mixture with high melting point, or mixing these derivatives with one or more other polymers and/or physiologically acceptable auxiliaries, and dissolving in a solvent or solvent mixture with high melting point, and adding dropwise to a condensed cold gas, for example liquid nitrogen. This results, owing to the Leidenfrost phenomenon, in absolutely round particles. Examples of solvents which can be employed are alcohols, dimethylformamide, dimethyl sulfoxide, tetrahydrofuran, methjylene chloride, dioxane, acetonitrile or mixtures with alcohols. The high-melting and water-miscible solvent is dissolved out, for example by transferring the microparticles into water, and the polymer is precipitated thereby, with retention of the spherical shape of the microparticles.

If the organic solvent which is used not only has a high melting point but also has a low boiling point, this dropwise addition process can be further simplified by the possibility of removing the solvent, for example tert-butanol, directly and under mild conditions by freeze-drying.

Another process for the preparation of the ultrasonic contrast agents comprises one or more of the polyaminodicarboxylic acid-co-imide derivatives of the formula I being dissolved in a solvent or solvent mixture and, where appropriate after addition of another solvent and/or of one or more further polymers, being precipitated or dispersed in water. Examples of other polymers which are suitable are polyvinyl alcohol (®Mowiol 28-99) or polyoxyethylene-polyoxypropylene (®Pluronic F 127). Ethers, for example, can be used as further solvents. Microparticles with a diameter of 0.5 to 15 μm are obtained by vigouous stirring, for example with a mixer (25,000 rpm). The solvents are subsequently removed, for example by lyophilization.

A particularly advantageous process comprises obtaining the microparticles by spray-drying. For this, one or more polyamino-dicarboxylic acid-co-imide derivatives of the formula I are dissolved, or these derivatives are mixed with one or more other polymers and/or physiologically acceptable auxiliaries and dissolved. Examples of suitable solvents or solvent mixtures are alcohol, dimethylformamide, dimethyl suylfoxide, tetrahydrofuran, methylene chloride, dioxane or acetonitrile. The solution is then sprayed to give microparticles in a spray drier.

The polymers of the formula I can be used alone or else as mixture of various polymers of the formula I in the described process. These polymers can also be employed in mixtures with other biodegradable and/or biocompatible polymers (for example ®Pluronic F68, PHEA, dextrans, polyethylene glycols, hydroxyethyl starch and other degradable or excretable polysaccharides) or physiologically acceptable auxiliaries (for example polymer plasticizers).

The microparticles contain gas, for example air, nitrogen, noble gases such as helium, neon, argon or krypton, hydrogen, carbon dioxide, oxygen or mixtures thereof. The microparticles are charged with a gas by, for example, the microparticles being stored in an appropriate gas atmosphere after the lyophilization or, in the case of spray-drying, are obtained directly on preparation in an appropriate gas atmosphere.

The ultrasonic contrast agents according to the invention are converted before administration into a suitable diagnostic or therapeutic administration form by addition of one or more physiologically acceptable vehicles and, where appropriate, further additives and/or auxiliaries. The ultrasonic contrast agents are, for example, suspended before administration by addition of water and mixing.

Physiological isotonicity of the particle suspension can be set up by addition of substances with osmotic activity, for example sodium chloride, galactose, glucose or fructose.

The described process for the preparation of the ultrasonic contrast agents according to the invention can result in particle sizes in which 90% of the particles are between 0.1 μm and 15 μm. Using the spray-drying process it is possible to obtain particle size distributions in which 90% of the particles are smaller than 3 μm. Larger particles are removed by screening out, for example with a 15 μm screen fabric and/or 3 μm screen fabric. When these microparticles are used as ultrasonic contrast agents for the diagnosis of cardiovascular disorders, particle sizes of 0.1 μm to 7 μm have proven suitable, and particle sizes of 0.1 μm to 3 μm are preferably employed. The ultrasonic contrast agents are injected, for example, into the blood circulation. Per injection, 0.1 mg to 1000 mg of the microparticles, preferably 1 mg to 100 mg, are employed.

The ultrasonic contrast agents described above can be used for both diagnostic and therapeutic procedures. The use of the ultrasonic contrast agents according to the invention is not confined just to the visualization of the blood flow in the right-ventricular part of the blood circulation after venous administration. The ultrasonic contrast agents can be used with exceptional success for investigating the left side of the heart and the myocardium. Furthermore, it is also possible to visualize other organs with a blood supply, such as the liver, spleen, kidney or brain, using these contrast agents.

The ultrasonic contrast agents according to the invention are, however, also suitable for the visualization of cavities in humans, animals or plants, for example the urinary bladder, ureter, uterus or vagina.

The invention is described in detail in the examples which follow. Unless otherwise indicated, percentages relate to weight.

EXAMPLE 1

Preparation of polysuccinimide-co-α, β-(hydroxyethyl)-D,L-aspartamide (70:30)

10 g (103 mmol) of polyanhydroaspartic acid are dissolved in about 40 ml of N,N-dimethylformamide (DMF), if necessary warming gently. To this solution are added dropwise 1.83 g (30 mmol) of freshly distilled 2-aminoethanol and stirred at room temperature overnight. The reaction mixture is precipitated in butanol and washed several times with dry acetone. The drying is carried out at elevated temperature in vacuo. The white, water-soluble product is obtained in approximately 100% yield and is examined by NMR spectroscopy for residues of DMF and butanol. The molar ratio of polyanhydroaspartic acid to aminoethanol employed corresponds approximately to the copolymer composition.

EXAMPLE 2

Preparation of n-butyl 4-chloro-4-oxobutyrate

Excess thionyl chloride and one drop of DMF are added to monobutyl succinate. The reaction takes place with evolution of gas. The mixture is left to stir with exclusion of moisture overnight and subsequently the excess thionyl chloride is removed by distillation under atmospheric pressure. The remaining crude product is fractionally distilled under 0.05 mbar, and the pure product is obtained at about 70° C. The characterization of the product by IR spectroscopy shows bands at 1800 cm$^{-1}$ (acid chloride) and 1740 cm$^{-1}$ (ester) of equal intensity.

EXAMPLE 3

Preparation of polysuccinimide-co-α, β-(butyloxycarbonylpropionyloxyethyl)-D,L-aspartamide (70:30)

6 g of polysuccinimide-co-α, β-(hydroxyethyl)-D,L-aspartamide (=16 mmol of hydroxyethyl groups), prepared as described in Example 1, are dissolved in 100 ml of dry N,N-dimethylformamide (DMF). Addition of 4 g (50 mmol) of pyridine is followed by cooling to 0° C. and addition, while stirring, of 4.8 g (25 mmol) of n-butyl 4-chloro-4-oxobutyrate (see Example 2) over the course of 15 minutes. The mixture is stirred overnight and precipitated in 0.5 l of ether. The precipitate is filtered off with suction and washed with ether, acetone, water, acetone and ether. The result is about 8 g of a white polymer with an approximately 100% degree of substitution (can be checked by NMR spectroscopy). The resulting polymer is soluble, for example, in acetonitrile with a trace of dimethyl sulfoxide (DMSO), in DMSO or DMF.

EXAMPLE 4

Preparation of polysuccinimide-co-α, β-(nonylcarbonyloxyethyl)-D,L-aspartamide (50:50)

6 g of a polysuccinimide-co-α, β-(hydroxyethyl)-D,L-aspartamide (50:50) (=24 mmol of hydroxyethyl groups), which was prepared in analogy to Example 1 from polyanhydroaspartic acid (MW=14000) and 2-aminoethanol (molar ratio 2:1), are dissolved in 100 ml of dry DMF, and 8 g (100 mmol) of dry pyridine are added and cooled to 0° C. 9.6 g of distilled decanoyl chloride are slowly added dropwise, and further operations are in analogy to Example 3. About 8 g of a white, completely substituted polymer (NMR check) which is soluble, for example, in dichloromethane and THF with, in each case, a trace of DMSO or in methanol/dichloromethane mixtures are obtained.

EXAMPLE 5

Preparation of polysuccinimide-co-α,β-(nonylcarbonyloxyethyl)-D,L-aspartamide of diverse copolymer composition and various molecular weights In analogy to Example 1, various polysuccinimide-co-α,β-(hydroxyethyl)-D,L -aspartamides of, inter alia, the compositions 70:30, 50:50 and 30:70 were prepared from polyanhydroaspartic acids of various molecular weights (MW=7000; about 13000; 30000) and reacted with decanoyl chloride as described in Example 4 to give the corresponding polysuccinimide-co-α, β-(nonylcarbonyloxyethyl)-D,L-aspartamides.

a)-polysuccinimide-co-α,β-(nonylcarbonyloxyethyl)-D,L-aspartamide (70:30) from polyanhydroaspartic acid (MW=7000); characterized by NMR b)-polysuccinimide-co-α,β-(nonylcarbonyloxyethyl)-D,L-aspartamide (70:30) from polyanhydroaspartic acid (MW=14000); characterized by NMR c)-polysuccinimide-co-α,β-(nonylcarbonyloxyethyl)-D,L-aspartamide (70:30) from polyanhydroaspartic acid (MW=30000); characterized by NMR d)-polysuccinimide-co-α,β-(nonylcarbonyloxyethyl)-D,L-aspartamide (30:70) from polyanhydroaspartic acid (MW=12000); characterized by NMR

EXAMPLE 6

Preparation of polysuccinimide-co-α,β-(octyloxycarbonyloxyethyl)-D,L-aspartamide (70:30)

6 g of polysuccinimide-co-α,β-(hydroxyethyl)-D,L-aspartamide (70:30) (=16 mmol of hydroxyethyl groups), prepared as described in Example 1 from polyanhydroaspartic acid, (MW=37000) and aminoethanol, are reacted in analogy to Example 3 with 4.8 g (25 mmol) of octyl chloroformate and worked up correspondingly. About 8 g of a white, completely substituted polymer which is soluble in THF or methanol/dichloromethane mixtures are obtained.

EXAMPLE 7

Preparation of polysuccinimide-co-α,β-(nonylcarbonyloxyethyl) -co-α,β-(hydroxyethyl)-D,L-aspartamide (60:20:20)

6 g of polysuccinimide-co-α,β-(hydroxyethyl)-D,L-aspartamide (60:40) (=20 mmol of hydroxyethyl groups), which was prepared in analogy to Example 1 from polyanhydroaspartic acid and 2-aminoethanol (molar ratio 6:4), are reacted in analogy to Example 3 with 2.3 g of decanoly chloride (=12 mmol). Because reaction was incomplete (relatively low excess of acid chloride), only half the free OH groups are esterified. The result is about 7 g of a white polymer. Microparticles of this substance show a firm consistency in water and are easily suspendible.

EXAMPLE 8

Preparation of polysuccinimide-co-α,β-(oleyloxyethyl) -D,L-aspartamide (10:90)

6 g of polysuccinimide-co-α,β-(hydroxyethyl)-D,L-aspartamide (10:90) (=40 mmol of hydroxyethyl groups), prepared in analogy to Example 1 with a 1:9 molar ratio of polyanhydroaspartic acid 2-aminoethanol, are reacted with 20 g of distilled oleyl chloride in analogy to Example 3. The heterogeneous reaction mixture becomes homogeneous on addition of dichloromethane. It is precipitated twice in methanol which is cooled to −20° C. The yellowish-colored polymer is thermoplastic.

EXAMPLE 9

Preparation of Microparticles 40 mg of polysuccinimide-co-α,β-(nonylcarbonyloxyethyl)-D,L-aspartamide (50:50) from Example 4 are dissolved in 1 ml of methylene chloride/methanol (proportion 50/1 by volume). The solution is introduced while stirring (800 rpm) into a beaker containing 60 ml of 0.1% by weight of aqueous polyvinyl alcohol solution (®Mowiol 28-99) which is saturated with 0.3 ml of methylene chloride/methanol (50/1). At the same time, the solution is finely dispersed with a mixer (25,000 rpm).

After 5 minutes, the contents are poured into a beaker containing 200 ml of water and stirred for 30 minutes (200 rpm). The supernatant water is decanted off and the microparticles are lyophilized (diameter after lyophilization:0.5 to 15 μm).

EXAMPLE 10

Preparation of Microparticles 80 mg of polysuccinimide-co-α,β-(octylcarbonyloxyethyl)-D,L-aspartamide (70:30) from Example 6 are dissolved at 50° C. in 1 ml of dimethyl sulfoxide, and 20 mg of hydroxypropylcellulose (®Klucel M.) are added. The solution of the two polymers is added dropwise, using a needle (disposable syringe, external diameter of needle 0.6 mm), to previously introduced liquid nitrogen (100 ml).

The resulting micropoarticles are transferred into 200 ml of water and extracted from remaining solvent for 2 hours. Excess water is decanted off, and the microparticles are lyophilized (diameter after lyophilization: 1–2 μm).

EXAMPLE 11

Preparation of Microparticles 4 g each of polysuccinimide-co-α,β-(octyloxycarbonyloxyethyl)-D,L -aspartamide (A) (Example 6) and polysuccinimide-co-α,β-(nonylcarbonyloxyethyl)-D,L-aspartamide (B) (Example 5 d) are made into 2% solutions in the solvents indicated in Table 1. The polymers are subsequently sprayed to give microparticles in a spray drier (Bëchi 190 mini spray drier supplied by Bëchi, West Germany).

TABLE 1

| | | Particle size | | |
| --- | --- | --- | --- | --- |
| Substance | Solvent | 10% smaller than | 50% smaller than | 90% smaller than |
| A | THF | 1.6 μm | 3.6 μm | 6.7 μm |
| B | CH₂Cl₂ | 2.4 μm | 3.6 μm | 6.7 μm |
| B | CH₂Cl₂/ methanol 3.6:1 (vol.) | 1.3 μm | 1.9 μm | 3.0 μm |
| B | CH₂Cl₂/ methanol 2:3 (vol.) | 1.2 μm | 1.8 μm | 2.6 μm |
| B | THF/methanol | 1.3 μm | 1.9 μm | 2.7 μm |

TABLE 1-continued

| Substance | Solvent | Particle size | | |
|---|---|---|---|---|
| | | 10% smaller than | 50% smaller than | 90% smaller than |
| | 3.6:1 (vol.) | | | |

The size distribution of the microparticles was determined in a Cilas 715 granulometer.

In each case, 30 mg portions of the microparticles prepared above are dispersed in 1.5 ml of suspension aid. The suspension aids are composed of 150 mg of dextran 40 (supplied by Roth, West Germany), 7.5 mg of polysorbate and 13.5 mg of NaCl in 1.5 ml of distilled water. The suspensions are filtered using screen fabrics (15 μm and 3 μm mesh width) and subsequently lyophilized. Before administration, the microparticles are suspended in water.

EXAMPLE 12

Echocardiographic Examination of Dog 30 mg of microparticles (prepared as in Example 11, substance B, $CH_2Cl_2$/methanol 2:3 (vol.)) are resuspended in 1.5 ml of distilled water using a glass rod. This suspension is injected into a peripheral vein using an injection syringe. An ultrasound emitter of an ultrasonic apparatus (Toshiba, FSH 160a, Japan) is held on the thorax of the experimental animal so that a typical cross-section through the right and left heart is obtained. As soon as the ultrasonic contrast agent reaches the right half of the heart it is possible to see on the monitor of the ultrasonic apparatus how the blood labeled by the contrast agent reaches the right atrium, then the right ventricle and subsequently leaves the heart again via the pulmonary artery. After passage through the lungs, the left half of the heart can be seen owing to the contrast agent. The ultrasonic contrast is of equal intensity before and after passage through the lungs so that it can be assumed that there is essentially complete retention of the air in the polymers and essentially loss-free transport of the microparticles to the left half of the heart.

We claim:

1. A method for visualizing organs comprising using a diagnostic or therapeutic agent, wherein said diagnostic or therapeutic agent comprises one or more ultasonic contrast agent composed of microparticles which contain a gas and a polyaminodicarboxylic acid-co-imide derivative of the formula I

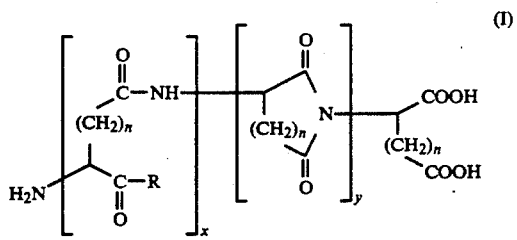

in which
n is 1 or 2
x is 1 to 500
y is 1 to 500, where
x+y is 2 to 1000, and
R is $O-R^1$ or $NH-R^2$, in which $R^2$ is H, $(CH_2)_m-OR^1$, $(CH_2)_m-O-C(O)-R^1$ or $(CH_2)_m-O-C(O)-OR^1$, and
m is 2 to 6, and
$R^1$ is H, aryl, aralkyl, arylalkenyl, alkyl or $C_3-C_8$-cycloalkyl or a biologically inactive steroid alcohol or an amino acid, where aryl is unsubstituted or is substituted by $C_1-C_4$-alkyl, $C_2-C_4$-alkenyl, $C_1-C_4$-alkylcarbonyloxy, $C_1-C_4$-alkoxy or hydroxyl,
where the alkyl radicals specified for $R^1$ have 1-22 carbon atoms and the alkenyl radicals have 2-22 carbon atoms, which are not interrupted or are interrupted by a carbonyloxy or oxycarbonyl group, where the repeating units placed in square brackets are distributed randomly and/or in blocks in the polymer, and where both the repeating units labeled with x and those labeled with y are identical or different and where the amino acids are α- and/or β-linked.

2. A method for investigating cavities in humans, animals or plants comprising using one or more diagnostic or therapeutic agent as defined in claim 1.

3. A method for diagnosing cardiovascular disorders comprising using one or more diagnostic or therapeutic agent as defined in claim 1.

* * * * *

UNITED STATES PATENT AND TRADEMARK OFFICE
CERTIFICATE OF CORRECTION

PATENT NO. : 5,205,287
DATED : April 27, 1993
INVENTOR(S) : Raimund Erbel et al.

It is certified that error appears in the above-indentified patent and that said Letters Patent is hereby corrected as shown below:

Claim 1, column 12, line 1, change "ultasonic" to --ultrasonic--.

Claim 1, column 12, line 30, before "$C_1$-$C_4$-alkoxy" insert --$C_1$-$C_4$-alkoxycarbonyl,--.

Signed and Sealed this

Fifth Day of July, 1994

Attest:

BRUCE LEHMAN

*Attesting Officer*   *Commissioner of Patents and Trademarks*